US010556026B2

(12) United States Patent
Bilenko et al.

(10) Patent No.: US 10,556,026 B2
(45) Date of Patent: Feb. 11, 2020

(54) ULTRAVIOLET TRANSPARENT STRUCTURE FOR ULTRAVIOLET ILLUMINATION

(71) Applicant: Sensor Electronic Technology, Inc., Columbia, SC (US)

(72) Inventors: Yuri Bilenko, Columbia, SC (US); Alexander Dobrinsky, Silver Spring, MD (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 19 days.

(21) Appl. No.: 15/911,698

(22) Filed: Mar. 5, 2018

(65) Prior Publication Data

US 2018/0193503 A1 Jul. 12, 2018

Related U.S. Application Data

(63) Continuation of application No. 15/015,539, filed on Feb. 4, 2016, now Pat. No. 9,907,869, which is a continuation of application No. 14/640,051, filed on Mar. 6, 2015, now Pat. No. 9,339,571.

(60) Provisional application No. 61/949,650, filed on Mar. 7, 2014.

(51) Int. Cl.
*A61L 2/10* (2006.01)

(52) U.S. Cl.
CPC ............. *A61L 2/10* (2013.01); *A61L 2202/14* (2013.01)

(58) Field of Classification Search
CPC ..... A61L 2/10; A61L 2/24; A61L 9/20; A23B 7/015; A23L 3/28; A61N 5/0624; B41J 11/002; E05B 1/0069
See application file for complete search history.

(56) References Cited

U.S. PATENT DOCUMENTS

| 6,490,351 B1 * | 12/2002 | Roberts ...................... A61L 2/10 379/439 |
| 7,553,456 B2 | 6/2009 | Gaska et al. |
| 8,277,734 B2 | 10/2012 | Koudymov et al. |
| (Continued) | | |

OTHER PUBLICATIONS

Purinton, B., U.S. Appl. No. 15/015,539, Notice of Allowance, dated Nov. 1, 2017, 11 pages.
(Continued)

*Primary Examiner* — Brooke Purinton
(74) *Attorney, Agent, or Firm* — LaBatt, LLC

(57) ABSTRACT

A solution for disinfecting a screen of an item using ultraviolet radiation is provided. The solution can provide an electronic device including a screen utilized by a user of the electronic device. The screen can be an ultraviolet transparent screen that covers at least some of the internal portion of the electronic device and a set of ultraviolet radiation sources can be located adjacent to the transparent screen. The set of ultraviolet radiation sources can be configured to generate ultraviolet radiation directed towards an external surface of the ultraviolet transparent screen. The electronic device can further include a monitoring and control system, which can manage the ultraviolet radiation generation by monitoring a set of attributes relating to the external surface of the screen and controlling, based on the monitoring, ultraviolet radiation directed at the external surface of the screen.

20 Claims, 11 Drawing Sheets

(56) References Cited

U.S. PATENT DOCUMENTS

| | | | |
|---|---|---|---|
| 8,384,047 B2 | 2/2013 | Shur et al. | |
| 8,431,910 B1 | 4/2013 | Perry | |
| 8,597,569 B2 | 12/2013 | Gruen et al. | |
| 9,042,967 B2* | 5/2015 | Dacosta | A61B 5/0059 |
| | | | 600/476 |
| 9,142,741 B2 | 9/2015 | Shatalov et al. | |
| 9,339,571 B2 | 5/2016 | Bilenko et al. | |
| 9,459,001 B2 | 10/2016 | Kjaer et al. | |
| 2002/0190220 A1 | 12/2002 | Sarchese et al. | |
| 2005/0072032 A1 | 4/2005 | McCollum et al. | |
| 2005/0184305 A1 | 8/2005 | Ueda | |
| 2005/0218468 A1* | 10/2005 | Owen | H01L 25/0753 |
| | | | 257/433 |
| 2006/0012285 A1 | 1/2006 | Matsumoto et al. | |
| 2006/0108910 A1 | 5/2006 | Justel et al. | |
| 2006/0195166 A1 | 8/2006 | Minamoto et al. | |
| 2006/0275188 A1 | 12/2006 | Wei | |
| 2009/0032527 A1 | 2/2009 | Lee et al. | |
| 2009/0280035 A1 | 11/2009 | Koudymov et al. | |
| 2010/0296971 A1 | 11/2010 | Gaska et al. | |
| 2011/0291995 A1 | 12/2011 | Shr et al. | |
| 2012/0037536 A1 | 2/2012 | Lonsdale, II et al. | |
| 2013/0004367 A1 | 1/2013 | Roberts | |
| 2013/0045132 A1 | 2/2013 | Tumanov | |
| 2013/0048545 A1 | 2/2013 | Shatalov et al. | |
| 2013/0063922 A1 | 3/2013 | La Porte et al. | |
| 2013/0255100 A1* | 10/2013 | Valia | F26B 3/347 |
| | | | 34/275 |
| 2013/0270445 A1 | 10/2013 | Gaska et al. | |
| 2014/0000844 A1 | 1/2014 | Chandaria | |
| 2014/0008675 A1 | 1/2014 | Shatalov et al. | |
| 2014/0016351 A1 | 1/2014 | Park et al. | |
| 2014/0050612 A1* | 2/2014 | Kneissl | A61L 2/10 |
| | | | 422/24 |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0061509 A1 | 3/2014 | Shur et al. | |
| 2014/0183377 A1 | 7/2014 | Bettles et al. | |
| 2014/0202962 A1 | 7/2014 | Bilenko et al. | |
| 2014/0264070 A1 | 9/2014 | Bettles et al. | |
| 2014/0264076 A1 | 9/2014 | Bettles et al. | |
| 2015/0143648 A1 | 5/2015 | Batey | |
| 2016/0151523 A1 | 6/2016 | Bilenko et al. | |
| 2019/0030196 A1 | 1/2019 | Bilenko et al. | |
| 2019/0098842 A1 | 4/2019 | Barber, III et al. | |

OTHER PUBLICATIONS

Purinton, B., U.S. Appl. No. 15/015,539, Non-Final Rejection, dated Apr. 21, 2017, 14 pages.

Purinton, B., U.S. Appl. No. 15/015,539, Final Rejection, dated Nov. 16, 2016, 15 pages.

Purinton, B., U.S. Appl. No. 15/015,539, Non-Final Rejection, dated Jul. 5, 2016, 21 pages.

Purinton, B., U.S. Appl. No. 14/640,051, Notice of Allowance, dated Jan. 25, 2016, 6 pages.

Purinton, B., U.S. Appl. No. 14/640,051, Final Office Action 1, dated Nov. 25, 2015, 21 pages.

Purinton, B., U.S. Appl. No. 14/640,051, Office Action 1, dated Aug. 31, 2015, 28 pages.

Lee, Dong Wook, International Application No. PCT/US2015/019086, International Search Report, dated May 29, 2015, 3 pages.

Chinese Application No. 201590000461.7, Notice of Allowance, dated Apr. 28, 2017, 2 pages. (English translation is not available.).

Chinese Application No. 201590000461.7, Office Actionl, dated Feb. 3, 2017, 2 pages. (English translation is not available.).

Purinton, B., U.S. Appl. No. 16/142,927, Notice of Allowance, dated Jun. 24, 2019, 9 pages.

* cited by examiner

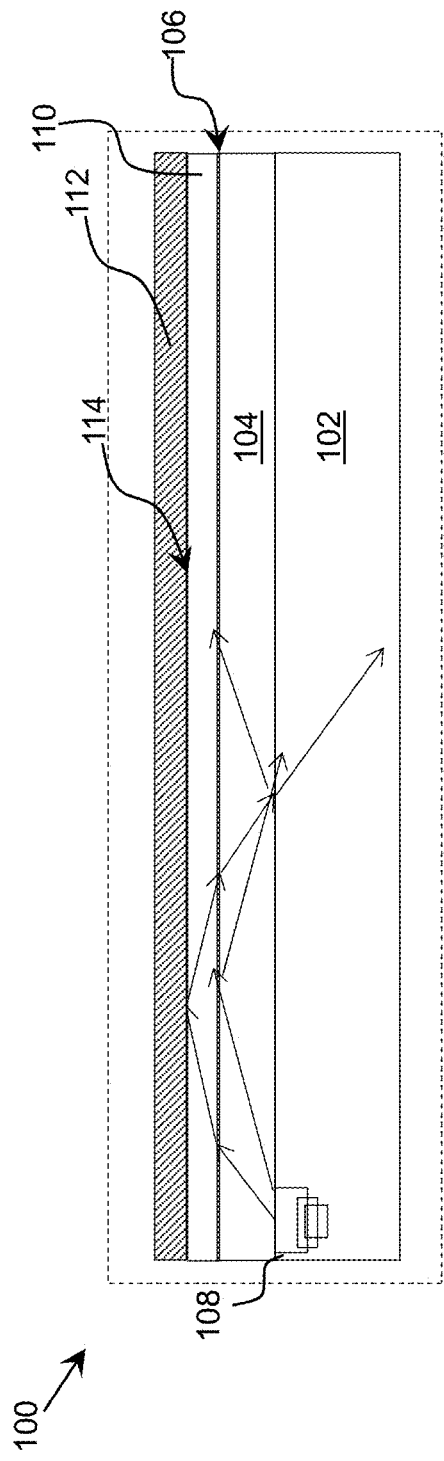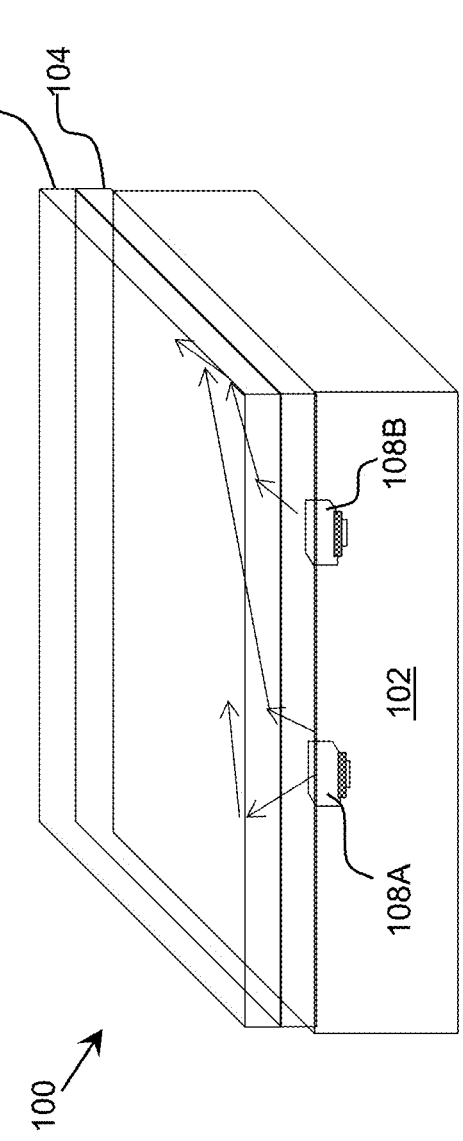
FIG. 1A
FIG. 1B

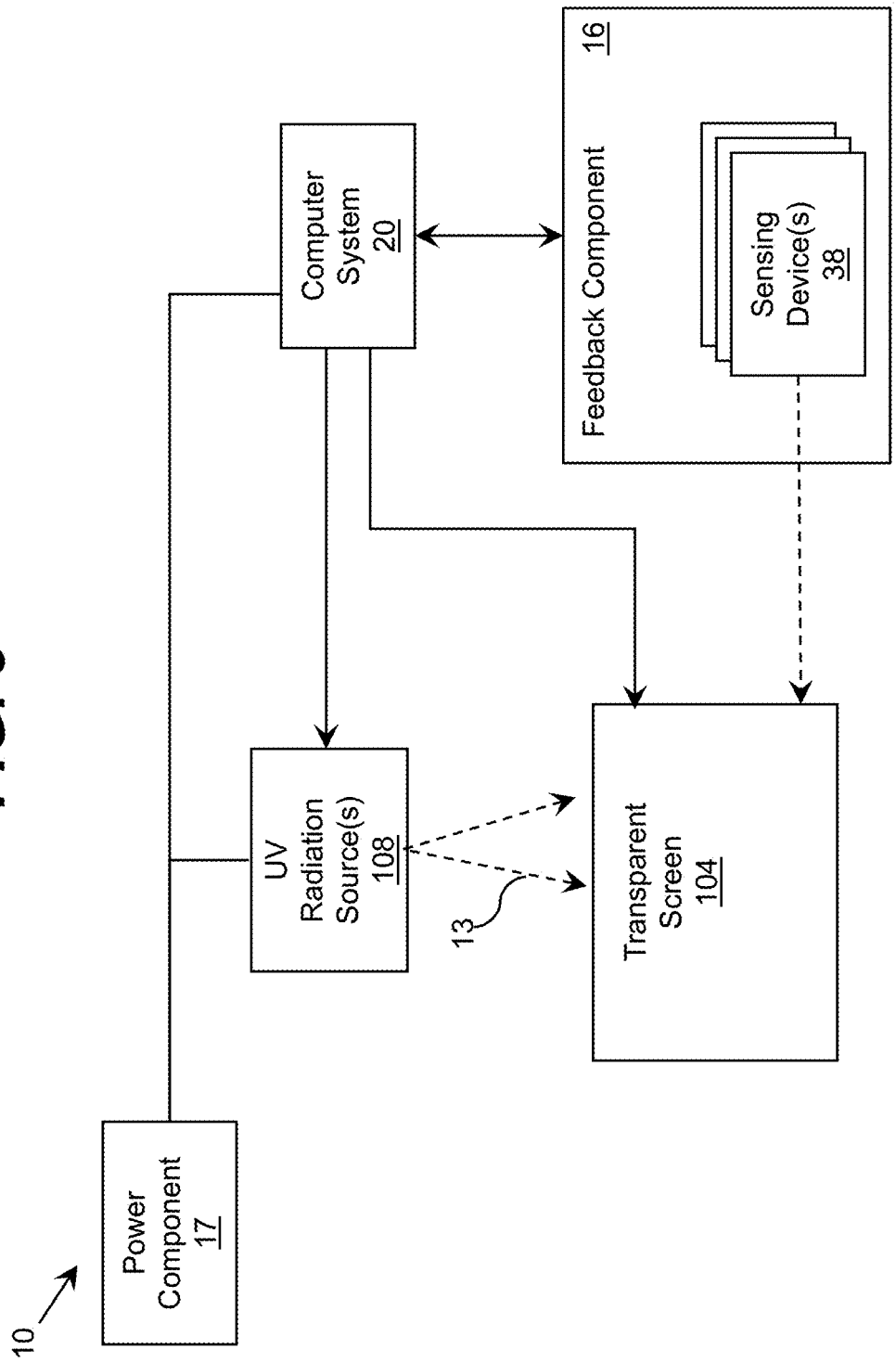

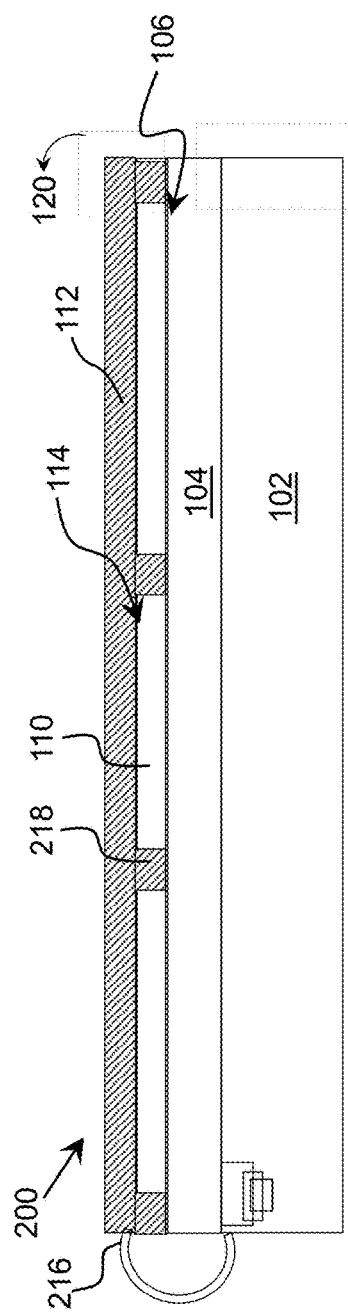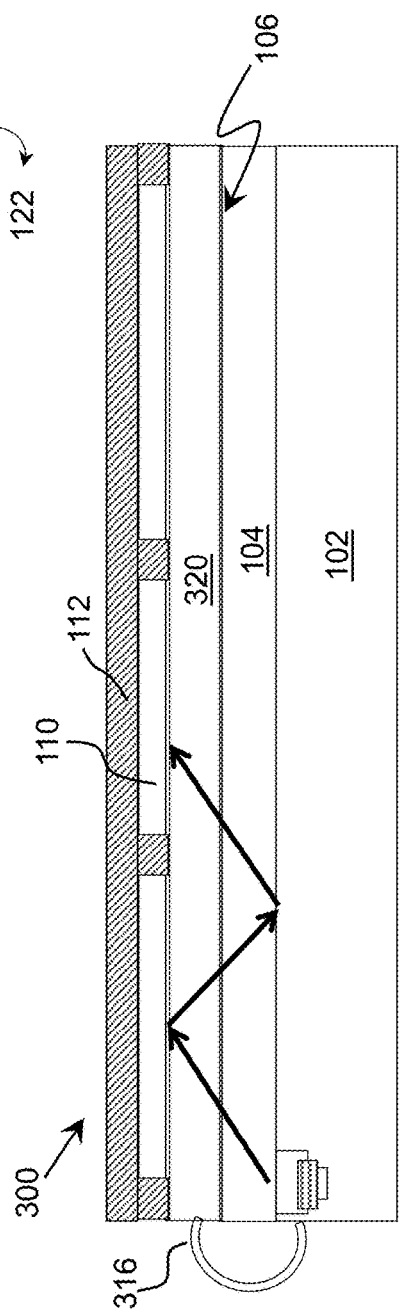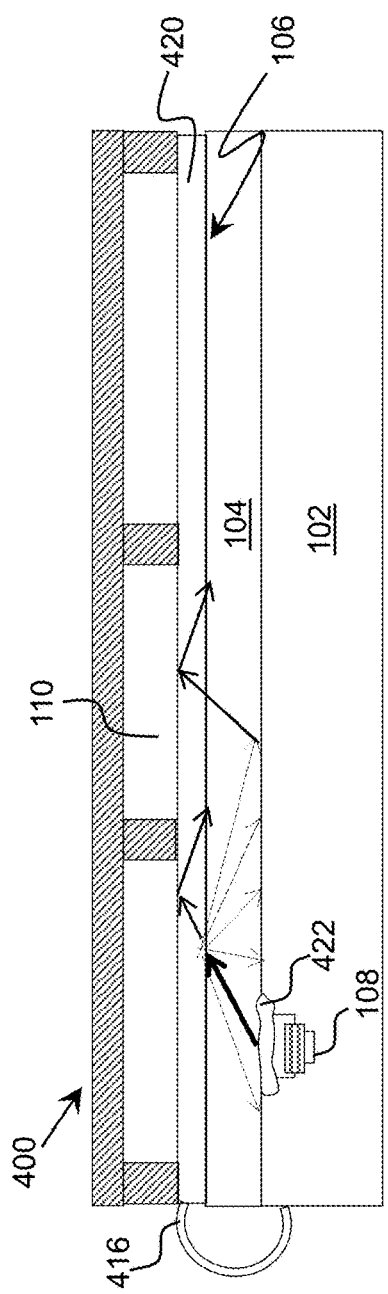

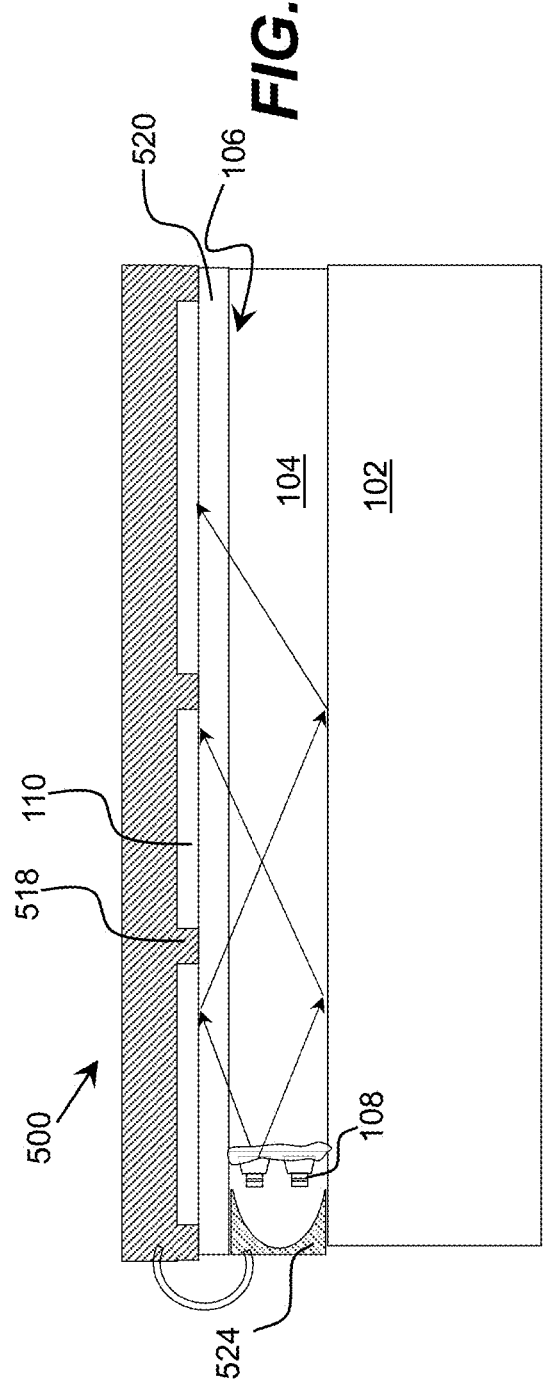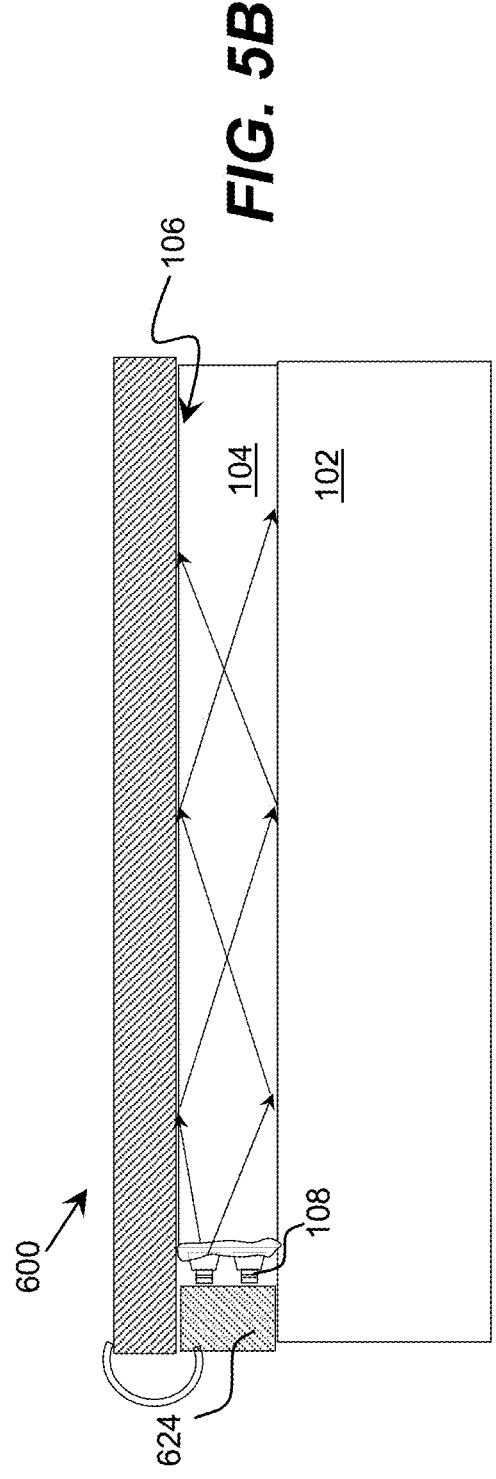

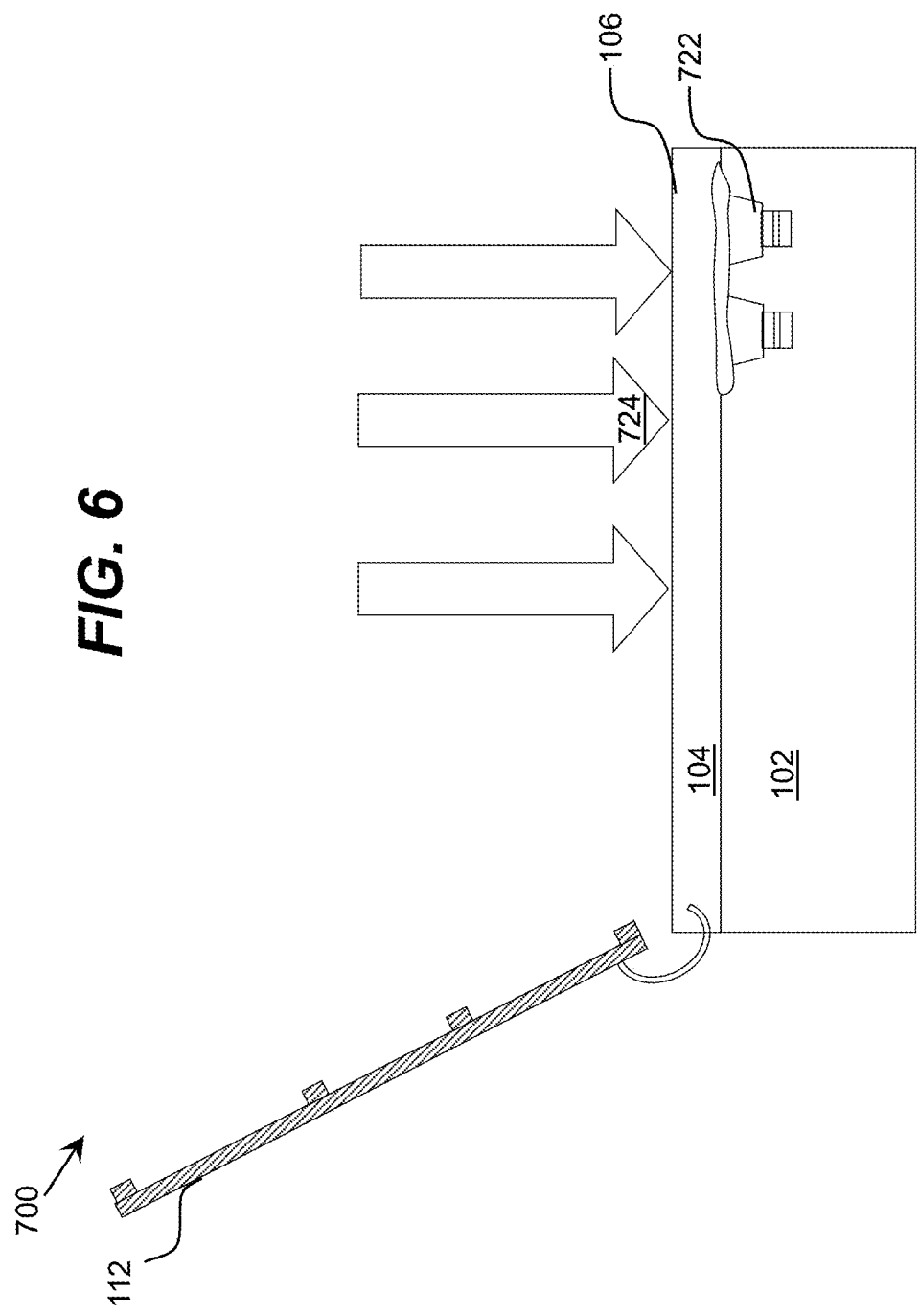

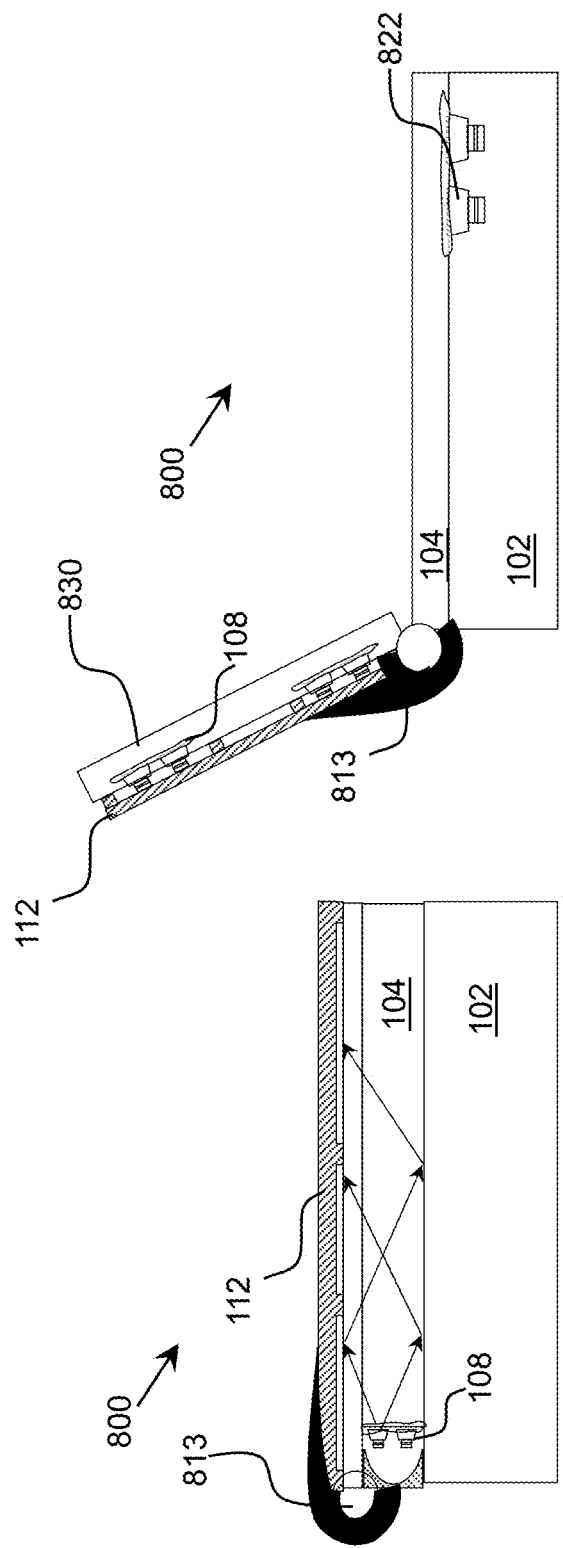
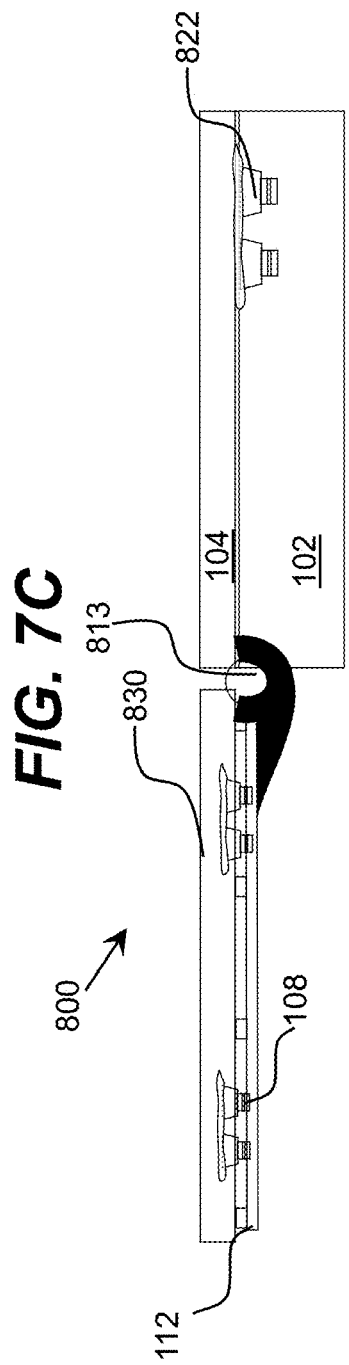

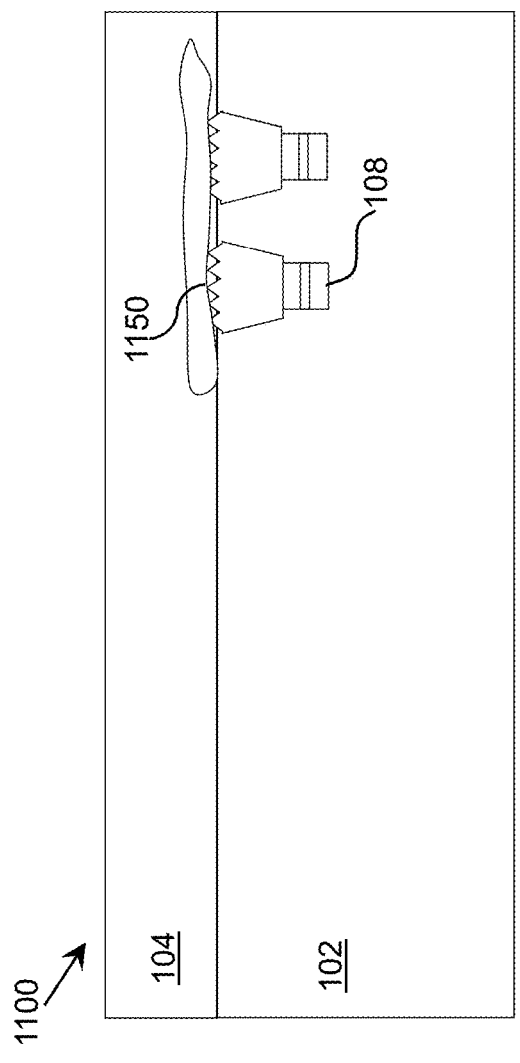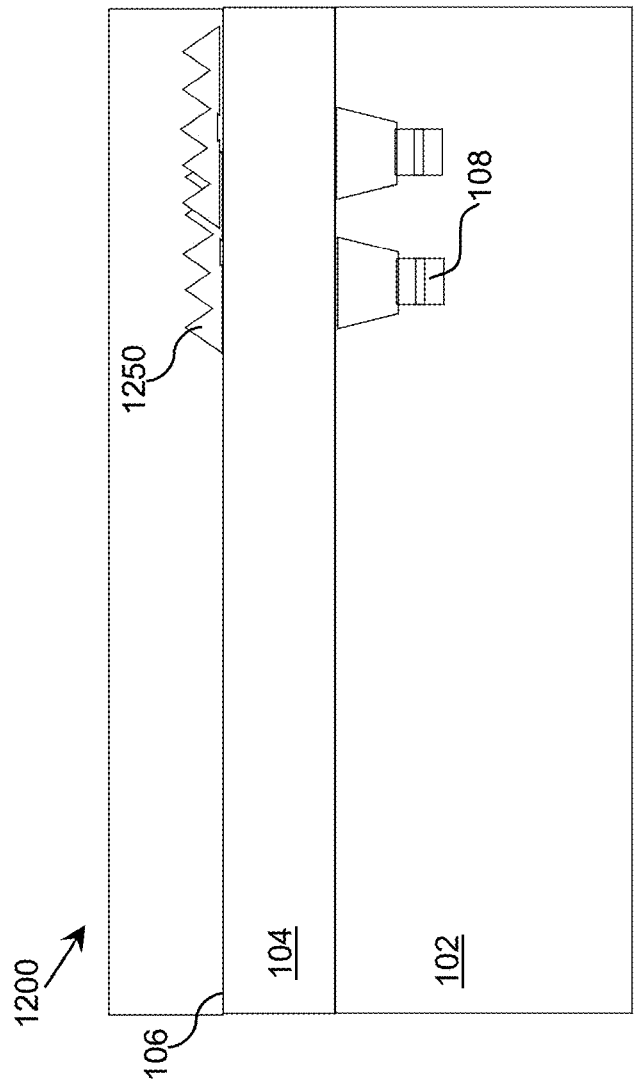

ULTRAVIOLET TRANSPARENT STRUCTURE FOR ULTRAVIOLET ILLUMINATION

REFERENCE TO RELATED APPLICATIONS

The current application is a continuation of U.S. patent application Ser. No. 15/015,539, filed on Feb. 4, 2016, which is a continuation of U.S. patent application Ser. No. 14/640,051, filed on Mar. 6, 2015, now U.S. Pat. No. 9,339,571, which claims the benefit of U.S. Provisional Application No. 61/949,650, filed on Mar. 7, 2014, each of which is hereby incorporated by reference. Aspects of the invention are related to U.S. patent application Ser. No. 13/517,711, filed on Jun. 14, 2012, now U.S. Pat. No. 9,142,741, which is hereby incorporated by reference.

TECHNICAL FIELD

The disclosure relates generally to ultraviolet illumination, and more particularly, to a solution for disinfecting the surface of an item using ultraviolet radiation.

BACKGROUND ART

Ultraviolet (UV) radiation has been utilized to sanitize different devices. For example, there is an approach for sanitizing toothbrushes using UV light. This approach relies on a UV lamp of low intensity for emitting UV radiation in the 200 to 300 nanometer wavelength range, as well as some radiation in the visible range above 300 nanometers and in the ozone producing range below 200 nanometers.

There are currently a number of UV devices available to sterilize mobile phones, such as the UV Sterilizer for the iPhone® from Sinco-Electronic Gifts Co. This UV Sterilizer is a desktop unit. A user places his/her phone into the sterilizer for approximately five minutes. The device turns a blue light emitting diode (LED) on to indicate the start of the sterilization process. Once the blue LED turns off, the sterilization process is complete. Many of such devices utilize mercury lamps to generate the ultraviolet light. However, UV LEDs have been proposed for use in many disinfection-related applications.

SUMMARY OF THE INVENTION

Aspects of the invention provide a solution for disinfecting the surface of a screen of an item using ultraviolet radiation. An embodiment of the solution can include an electronic device including a screen utilized by a user of the electronic device. The screen can be an ultraviolet transparent screen that covers at least some of the internal portion of the electronic device and a set of ultraviolet radiation sources can be located adjacent to the transparent screen. The set of ultraviolet radiation sources can be configured to generate ultraviolet radiation directed towards an external surface of the ultraviolet transparent screen. The electronic device can further include a monitoring and control system, which can manage the ultraviolet radiation generation by monitoring a set of attributes relating to the external surface of the screen and controlling, based on the monitoring, ultraviolet radiation directed at the external surface of the screen.

A first aspect of the invention provides an apparatus comprising: an ultraviolet transparent screen, wherein an external surface of the ultraviolet transparent screen is accessible to a user of the apparatus; a set of ultraviolet radiation sources located adjacent to at least one of: an internal surface or a side of the transparent screen, the set of ultraviolet radiation sources configured to generate ultraviolet radiation directed towards the external surface of the ultraviolet transparent screen; and a monitoring and control system located in an internal portion of the apparatus for managing the ultraviolet radiation by performing a method comprising: monitoring a set of attributes relating to the external surface of the ultraviolet transparent screen; and controlling, based on the monitoring, the ultraviolet radiation directed at the external surface of the ultraviolet transparent screen.

A second aspect of the invention provides an electronic device comprising: an internal portion for containing electronic components of the electronic device; an ultraviolet transparent screen covering at least a portion of the internal portion; a set of ultraviolet radiation sources adjacent to the transparent screen, the set of ultraviolet radiation sources configured to generate ultraviolet radiation to disinfect an external surface of the ultraviolet transparent screen; a cover configured to removably cover the external surface of the ultraviolet transparent screen; and a monitoring and control system for managing the set of ultraviolet radiation sources by performing a method comprising: monitoring a plurality of attributes for the cover and the external surface of the ultraviolet transparent screen; and controlling, based on the monitoring, the ultraviolet radiation directed at the external surface of the ultraviolet transparent screen.

A third aspect of the invention provides a device comprising: an internal portion containing a set of electronic components of the device; an ultraviolet transparent screen covering at least a portion of the internal portion; a set of ultraviolet radiation sources epitaxially grown on an internal surface of the ultraviolet transparent screen, the set of ultraviolet radiation sources configured to generate ultraviolet radiation directed towards an external surface of the ultraviolet transparent screen; and a cover configured to removably cover the ultraviolet transparent screen.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 1A-1B show cross-sectional views of an illustrative device according to an embodiment.

FIG. 3 shows an illustrative system according to an embodiment.

FIGS. 4A-4C show cross-sectional views of an illustrative device according to an embodiment.

FIGS. 5A-5B show cross-sectional views of an illustrative device according to an embodiment.

FIG. 6 shows a cross-sectional view of an illustrative device according to an embodiment.

FIGS. 7A-7C show cross-sectional views of an illustrative device according to an embodiment.

FIGS. 11A-11B show cross-sectional views of an illustrative device according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2:
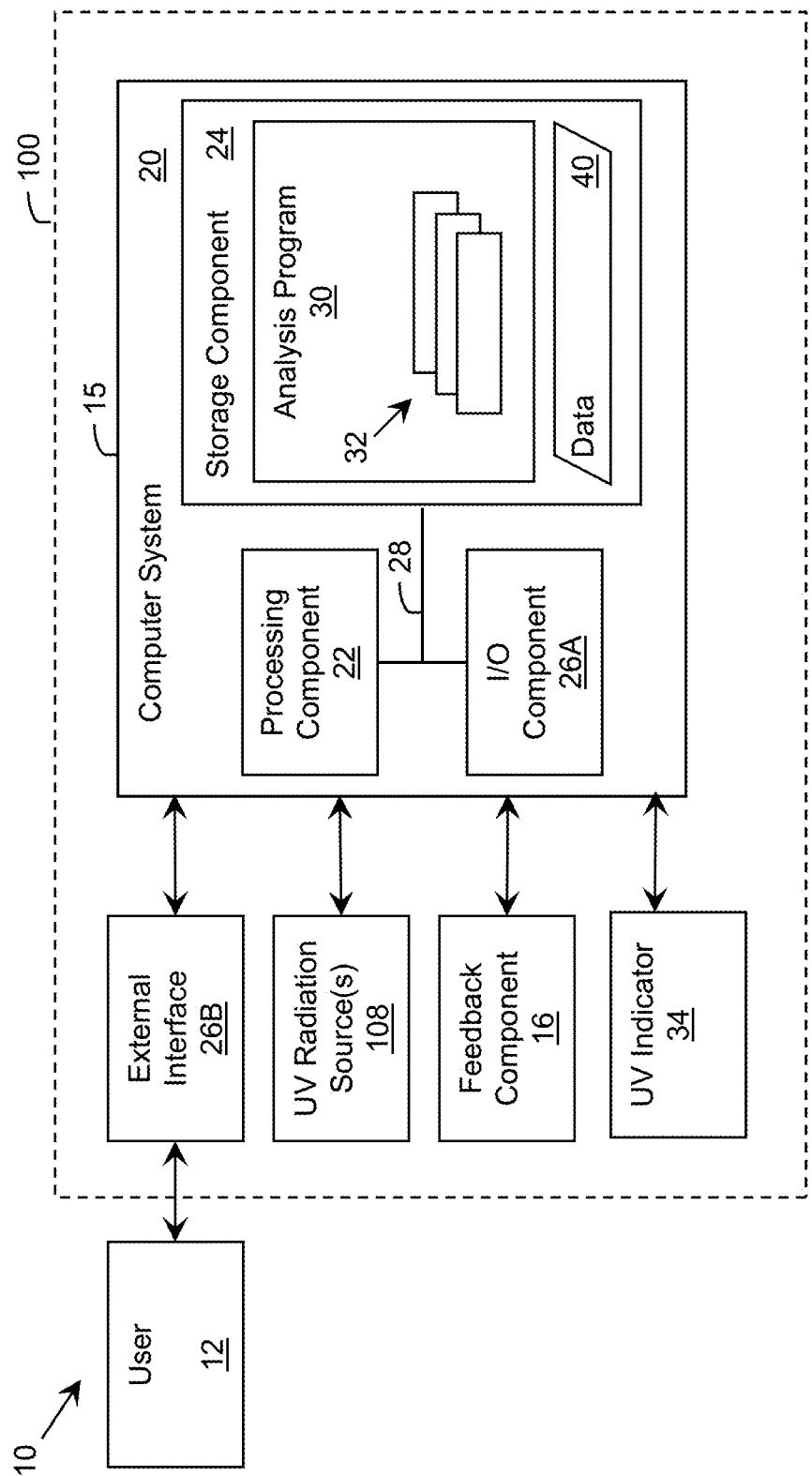
FIG. 2 shows an illustrative environment according to an embodiment.

As indicated above, aspects of the invention provide a solution for disinfecting a screen of an item using ultraviolet radiation. An embodiment provides an electronic device including a screen utilized by a user of the electronic device. The screen can be an ultraviolet transparent screen that covers at least some of the internal portion of the electronic device and a set of ultraviolet radiation sources can be located adjacent to the transparent screen. The set of ultraviolet radiation sources can be configured to generate ultraviolet radiation directed towards an external surface of the ultraviolet transparent screen. The electronic device can further include a monitoring and control system, which can manage the ultraviolet radiation generation by monitoring a set of attributes relating to the external surface of the screen and controlling, based on the monitoring, the ultraviolet radiation directed at the external surface of the screen.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through at a normal incidence to an interface of the material/structure. As used herein, unless otherwise noted, the term "set" means one or more (i.e., at least one) and the phrase "any solution" means any now known or later developed solution.

Furthermore, as used herein, the term "disinfection" and its related terms means treating a device and/or item so that it includes a sufficiently low number of contaminants (e.g., chemical) and microorganisms (e.g., virus, bacteria, and/or the like) so that the device and/or item can be handled as part of a desired human interaction with no or no reasonable risk for the transmission of a disease or other harm to the human. For example, disinfection of the device and/or item means that the device and/or item has a sufficiently low level of active microorganisms and/or concentration of other contaminants that a typical human can interact with the device and/or item without suffering adverse effects from the microorganisms and/or contaminants present on the device and/or item. In addition, disinfection can include sterilization. As used herein, the term "sterilization" and its related terms means neutralizing an ability of a microorganism to reproduce, which may be accomplished without physically destroying the microorganism. In this example, a level of microorganisms present on the device and/or item cannot increase to a dangerous level and will eventually be reduced, since the replication ability has been neutralized. A target level of microorganisms and/or contaminants can be defined, for example, by a standards setting organization, such as a governmental organization.

Turning to the drawings, FIG. 1A shows a cross-sectional view of a device 100 according to an embodiment. The device 100 can include any type of handheld electronic gadget, such as a mobile phone, a tablet, a laptop, and/or the like. In this case, the device 100 includes an internal portion 102 for containing electronic components of the electronic gadget. An ultraviolet transparent screen 104 is located on top of the internal portion 102 and can be formed of any ultraviolet transparent material, such as fused silica, sapphire, quartz, an ultraviolet transparent polymer, and/or the like. In an embodiment, the transparent screen 104 can include at least one ultraviolet transparent polymer, such as, for example, fluorinated ethylene propylene (FEP), fluorinated ethylene propylene co-polymer (EFEP), polyactic acid (PLA), low-density polyethylene (LDPE), and/or the like. In particular, these materials are sufficiently transparent to transmit ultraviolet radiation of certain wavelengths. The transparent screen 104 includes a top surface 106 which is accessible to a user of the electronic gadget and would require disinfection. In an embodiment, the ultraviolet transparent screen 104 is formed of a material that is transparent and includes a refractive index that is similar to sapphire, wherein similar is within approximately 30% of the refractive index of sapphire. In an embodiment, the ultraviolet transparent screen 104 can be discontinuous and cover between approximately 5% to approximately 90% of the lateral area of the internal portion 102 of the device 100.

The device 100 can include a set of ultraviolet radiation sources 108 located in the internal portion 102 of the device 100, which can be placed adjacent to the ultraviolet transparent screen 104. In FIG. 1A, only one ultraviolet radiation source 108 is shown for illustrative purposes and it is understood that any number of ultraviolet radiation sources 108 may be located within the device 100. For example, in FIG. 1B, the device 100 is shown including a first ultraviolet radiation source 108A and a second ultraviolet radiation source 108B. It is understood that certain layers (e.g., layer 110) can be omitted from the device 100 (e.g., in FIG. 1B). The set of ultraviolet radiation sources 108 can comprise any combination of one or more ultraviolet radiation emitters. For example, the set of ultraviolet radiation sources 108 can include a high intensity ultraviolet lamp (e.g., a high intensity mercury lamp), a discharge lamp, an ultraviolet light emitting diode (LED), super luminescent LEDs, laser diodes, and/or the like. In an embodiment, the set of ultraviolet radiation sources 108 includes a set of light emitting diodes manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet radiation sources 108 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, towards the transparent screen 104. Illustrative wave guiding structures include, but are not limited to, a plurality of ultraviolet fibers, each of which terminates at an opening, a diffuser, and/or the like.

As illustrated in FIG. 1A, a layer 110 including a refractive index that is lower than the refractive index of the ultraviolet transparent screen 104 can be located on top of the ultraviolet transparent screen 104. In an embodiment, the refractive indexes are selected to increase an amount of total internal reflection (TIR) of the ultraviolet radiation that occurs at a boundary between the layer 110 and the ultraviolet transparent screen 104. For example, in an embodiment, the layer 110 can include ambient air. The device 100 can further include a cover 112 located on top of the layer 110. The cover 112 can include a reflective surface 114, which is configured to reflect ultraviolet radiation in a direction of the top surface 106 of the transparent screen 104.

The reflective surface 114 can include a material that is at least 50% reflective to radiation at a normal incidence. In an embodiment, the reflective surface 114 is at least 70% reflective. The reflective surface 114 can be formed of any type of reflective material. For example, illustrative ultraviolet reflective materials include: polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. The cover 112 also can include a layer of material that has antibacterial properties, such as titanium dioxide ($TiO_2$), which can assist in sterilization and disinfection and is activated by light.

FIGS. 1A and 1B show illustrative examples of ultraviolet radiation emitted from the set of ultraviolet radiation sources 108. The ultraviolet radiation can be transmitted through the transparent screen 104 and reflected at the top surface 106 of the transparent screen 104 by total internal reflection (TIR) and/or off the reflective surface 114 in order to disinfect the top surface 106 of the transparent screen 104. The ultraviolet radiation can continue to be transmitted through the transparent screen 104 and reflect off a surface of the internal portion 102, so that ultraviolet radiation is recycled within the device 100.

Turning now to FIG. 2, an illustrative ultraviolet radiation system 10 according to an embodiment is shown. In this case, the system 10 includes a monitoring and/or control system 15 incorporated in the device 100, which is shown implemented as a computer system 20 including an analysis program 30, which makes the computer system 20 operable to manage an ultraviolet radiation source 108 by performing a process described herein. In particular, the analysis program 30 can enable the computer system 20 to operate the ultraviolet radiation source(s) 108 to generate and direct ultraviolet radiation toward the top surface 106 of the transparent screen 104 of the device 100 (FIG. 1A) and process data corresponding to one or more attributes regarding the device 100, which is acquired by a feedback component 16, and/or an ultraviolet radiation history stored as device data 40. While a single ultraviolet radiation source 108 is shown in this figure, it is understood that the device 100 can include any number of ultraviolet radiation sources 108, the operation of which the computer system 20 can separately manage using a process described herein. In the case of more than one ultraviolet radiation source 108 (e.g., as shown in FIG. 1B), it is understood that the computer system 20 can individually control each ultraviolet radiation source 108 and/or control two or more of the ultraviolet radiation sources 108 as a group. Furthermore, the ultraviolet radiation sources can emit ultraviolet radiation of substantially the same wavelength or of multiple distinct wavelengths.

In an embodiment, during an initial period of operation (e.g., while the cover 112 is placed over the transparent screen 104 (FIG. 1A), and/or the like), the computer system 20 can acquire data from the feedback component 16 regarding one or more attributes of the device 100 and generate data 40 for further processing. The data 40 can include a presence of biological activity (e.g., microorganisms, viruses, bacteria, and/or the like) on the top surface 106, a frequency of usage of the electronic gadget of the device 100, a disinfection schedule history for the device 100, an amount of radiation (e.g., ultraviolet, infrared, visible, and/or microwave), and/or the like. The computer system 20 can use the data 40 to control one or more aspects of the ultraviolet radiation generated by the ultraviolet radiation source(s) 108.

Furthermore, one or more aspects of the operation of the ultraviolet radiation source 108 can be controlled by a user 12 via an external interface component 26B. The external interface component 26B can be located on the top surface 106 (FIG. 1A) and allow the user 12 to choose when to turn on the ultraviolet radiation source 108. However, it is understood that, in order to turn on the ultraviolet radiation source 108, the computer system 20 can first determine that the cover 112 is over the remaining portions of the device 100 to avoid harming the user 12, e.g., using data acquired by the feedback component 16. The external interface component 26B can include a touch screen that can selectively display user interface controls, such as control dials, which can enable the user 12 to adjust one or more of: an intensity, scheduling, and/or other operational properties of the set of ultraviolet radiation sources 108. In an embodiment, the external interface component 26B can include a keyboard, a plurality of buttons, a joystick-like control mechanism, and/or the like, which can enable the user 12 to control one or more aspects of the operation of the set of ultraviolet radiation sources 108.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 12 to interact with the computer system 20 and/or one or more communications devices to enable a system user 12 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 12 to interact with the analysis program 30. Furthermore, the analysis program 30 can manage (e.g., store, retrieve, create, manipulate, organize, present, etc.) the data, such as data 40, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 15 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 15.

Regardless, when the computer system 20 includes multiple computing devices, the computing devices can communicate over any type of communications link. Furthermore, while performing a process described herein, the computer system 20 can communicate with one or more other computer systems, such as the user 12, using any type of communications link. In either case, the communications link can comprise any combination of various types of wired and/or wireless links; comprise any combination of one or more types of networks; and/or utilize any combination of various types of transmission techniques and protocols.

The system 10 also can include an ultraviolet radiation indicator 34 (e.g., an LED), which can be operated by the computer system 20 to indicate when ultraviolet radiation is being generated within the device 100. The ultraviolet radiation indicator 34 can include one or more LEDs for emitting a visual light for the user 12. In another embodiment, the indicator 34 can be an alarm (e.g., an auditory signal) for signaling that ultraviolet radiation is being generated.

Turning now to FIG. 3, an illustrative system including an ultraviolet radiation system 10 for disinfecting the transparent screen 104 (FIG. 1A) is shown. The computer system 20 is configured to control the ultraviolet radiation source 108 to direct ultraviolet radiation 13 at the transparent screen 104 as described herein. The feedback component 16 is configured to acquire data used by the computer system 20 to monitor a set of attributes regarding the device 100 over a period of time. As illustrated, the feedback component 16 can include a plurality of sensing devices 38, each of which can acquire data used by the computer system 20 to monitor the set of attributes.

It is understood that the set of attributes for the device 100 can include any combination of one or more of: a frequency of the usage of the device 100, a presence of biological activity on the transparent screen 104, a usage of the device 100, a disinfection schedule history for the device 100, and/or the like. In the case of determining usage details for the device 10, a sensing device 38 can include a sensor and/or a switch to sense that the cover 112 is over the remaining portion of the device 100. If the sensing device 38 senses that the cover 112 is not over the remaining portion of the device 100, the computer system 20 can either terminate the ultraviolet radiation 13 generated by set of ultraviolet radiation sources 108 and/or fail to turn on the set of ultraviolet radiation sources 108.

In the case of determining a presence of biological activity on the transparent screen 104 of the device 100, the sensing devices 38 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the sensing device 38 can determine information on the variation of the biological activity over time, such as a growth rate, a rate with which an area including the biological activity is spreading, and/or the like. In an embodiment, a set of biological activity dynamics are related to various attributes of bacteria and/or virus activity present on the transparent screen 104, including, for example, the presence of detectable bacteria and/or virus activity, measured bacteria and/or virus population/concentration time dynamics, growth phase, and/or the like.

In an embodiment, to determine the presence of biological activity on the transparent screen 104, the sensing devices 38 include at least one of a visual camera or a chemical sensor. The visual camera can acquire visual data (e.g., visual, electronic, and/or the like) used to monitor the transparent screen 104, while the chemical sensor can acquire chemical data (e.g., chemical, electronic, and/or the like) used to monitor the transparent screen 104. For example, when the computer system 20 is operating the ultraviolet radiation source 108, a visual camera and/or a chemical sensor 36 monitoring the transparent screen 104 may be operated to detect the presence of microorganisms. In a specific embodiment, the visual camera comprises a fluorescent optical camera that can detect bacteria and/or viruses that become fluorescent under ultraviolet radiation. However, it is understood that a visual camera and a chemical sensor are only illustrative of various types of sensors that can be implemented. For example, the sensing devices 38 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the transparent screen 104.

The computer system 20 can be configured to control and adjust a direction, an intensity, a pattern, and/or a spectral power (e.g., wavelength) of the set of ultraviolet radiation sources 108, based on data received from the feedback component 16. The computer system 20 can control and adjust each property of the set of ultraviolet radiation sources 108 independently. For example, the computer system 20 can adjust the intensity, time duration, and/or time scheduling (e.g., including duration (e.g., exposure/illumination time)), duty cycle, time between exposures/illuminations, and/or the like) of the ultraviolet radiation source 108 for a given wavelength. Each of the properties of the ultraviolet radiation source 108 can be adjustable and controlled by the computer system 20 according to data provided by the feedback component 16.

For example, the computer system 20 can be configured to adjust the direction of the ultraviolet radiation according to a location of the biological activity detected on the transparent screen 104 by the sensing device(s) 38 using any solution. The computer system 20 can be configured to utilize a target timing, intensity, and/or spectral power of the ultraviolet radiation 13 according to a type of biological activity. That is, the sensing devices 38 can sense locations of higher levels of biological activity on the transparent screen 104, and the ultraviolet radiation source 108 can be configured by the computer system 20 to direct higher doses (by increasing intensity or exposure) of ultraviolet radiation at the locations with higher levels of biological activity (e.g., non-uniform ultraviolet radiation).

The sensing devices 38 can also sense whether or not the cover 112 (FIG. 1A) is on and covering the remaining portion of the device 100. In response to detection of the cover 112 being present on the remaining portion of the device 100, the computer system 20 can be configured to automatically turn on the ultraviolet radiation 13. In one embodiment, the computer system 20 can be configured to set a periodic or an aperiodic schedule for the ultraviolet radiation when the cover 112 is in place. This (periodic or aperiodic) schedule can be interrupted when the sensing device 38 senses that the cover 112 is removed from the device 100 and the computer system 20 can be configured to turn off the ultraviolet radiation. In this case, the schedule (periodic or aperiodic) can be resumed once the sensing device 38 senses the cover 112 is in place.

The sensing device 38 can also include a radiation detector for detecting an amount of radiation that the top surface 106 is exposed to. The radiation can include any type of radiation, including, for example, ultraviolet, visible, infrared, microwave, and/or the like. The amount of radiation that the top surface 724 is exposed to can be used by the computer system 20 to determine if any additional radiation is required to disinfect the top surface 106.

It is understood that the system 10 may include a power component 17 that is implemented to supply power to one or more of the various components of system 10, such as the ultraviolet radiation source(s) 108, feedback component 16, computer system 20, and/or the like. For example, the device 100 (FIG. 1A) may comprise a power source that is insufficient to operate the various devices of system 10 in addition to maintaining sufficient power to continue one or more aspects of the operation of the device 100. Regardless, the power component 17 can be utilized to operate system 10. The power component 17 can be embedded in the internal portion 102 (FIG. 1A) of the device 100 along with the set of ultraviolet radiation sources 108. The power component 17 can comprise any source of power including, but not limited to, a battery set, a solar cell, and/or the like. For example, the power component 17 can include any of various types of rechargeable batteries (e.g., lithium ion, nickel-cadmium, and/or the like). The power component 17 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a Universal Serial Bus (USB) connection. In another embodiment, heat from a user provides power to the power component 17. In an embodiment, the power component 17 and/or other electronic components (e.g., computer system 20, feedback component 16, and/or the like) can be grown and monolithically integrated on a sapphire surface of the internal portion 102 (FIG. 1A).

Turning now to FIGS. 4A-4C, cross-sectional views of illustrative devices 200, 300, 400 according to embodiments are shown. In FIG. 4A, the device 200 is similar to the device 100 shown in FIG. 1A. However, the device 200 can include a hinge 216 coupled to the cover 112 and a portion of the device 200. The portion can be either the internal portion 102, the transparent screen 104, and/or the like. The hinge 216 is used to open and close the cover 112. The hinge 216 can enable movement of the cover 112 and a remaining portion of the device 200 away from one another in the direction of arrows 120, 122. It is understood that the hinge 216 shown in FIGS. 4A-4C is only illustrative of various mechanisms that can be utilized for opening and closing the cover 112. For example, the cover 112 can slide on and off the device 200 using a track, be magnetically attached to the device 100, and/or the like. In the embodiment where the cover 112 can slide on and off of the device 200, the sliding motion can result in the top surface 106 of the ultraviolet transparent screen 104 being wiped. In this embodiment, the reflective surface 114 (FIG. 1A) of the cover 112 can include a material for wiping the top surface 106 of the ultraviolet transparent screen 104. The cover 112 can also contain an antibacterial liquid that is released during the sliding/wiping motion of the cover 112. Examples of antibacterial liquids include alcohols, triclosan, triclocarban, chloroxylenol and/or the like. The cover 112 can include a plurality of fins 218 of substantially the same height and width. The plurality of fins 218 extend from the cover 112 into the layer 110 (e.g., air) and touch the top surface 106 of the transparent screen 104. The plurality of fins 218 can provide a boundary between the cover 112 and the transparent screen 104.

In FIG. 4B, the device 300 can include an additional ultraviolet transparent layer 320 located above the transparent screen 104. The ultraviolet radiation generated by the ultraviolet radiation source 108 can transmit through both the transparent screen 104 and the additional ultraviolet transparent layer 320. A difference in the refractive indices at the interface of the layer 110 (e.g., air) and the additional ultraviolet transparent layer 320 can reflect the ultraviolet radiation back towards the transparent screen 104, as shown by the arrows in FIG. 4B. In this manner, the top surface 106 of the transparent screen 104 can be disinfected. In an embodiment, the additional ultraviolet transparent layer 320 can be formed of an ultraviolet transparent material with a refractive index that is higher than the refractive index of the layer 110. The refractive index of the additional ultraviolet transparent layer 320 can be substantially similar or the same as the refractive index of the transparent screen 104. For example, when the layer 100 includes air, the additional ultraviolet transparent layer 320 and/or the transparent screen 104 can be formed of fused silica, sapphire, and/or the like. In this embodiment, the hinge 316 (or other mechanism) can be coupled to the additional ultraviolet transparent layer 320, instead of the cover 112 as shown in FIG. 4A, so that both the cover 112 and the additional ultraviolet transparent layer 320 are removed or opened by the hinge 316 to enable access to the surface 106 by a user.

In FIG. 4C, the device 400 can include a diffusively reflective layer 420. The diffusively reflective layer 420 can also be partially transmitting. The diffusively reflective layer 420 can include a diffusive reflection of at least approximately 30% of radiation at a normal incidence. The diffusively reflective layer 420 can be formed by an ultraviolet reflective material, including polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. The ultraviolet radiation generated by the ultraviolet radiation source 108 is diffusively reflected by the diffusively reflective layer 420, but can also be partially transmitted by the diffusively reflective layer 420, as shown by the arrows in FIG. 4C. The ultraviolet radiation that is transmitted by the diffusively reflective layer 420 can be reflected by the interface between the layer 110 and the diffusively reflective layer 420, so that the top surface 106 of the transparent screen 104 is disinfected.

An ultraviolet radiation source 108 can be attached to the device 100 using any known method. For example, the ultraviolet radiation source 108 can be grown on a sapphire substrate through epitaxy and the sapphire substrate can be utilized as the screen of the device 100 as it constitutes a transparent and scratch resistant material. In another embodiment, the ultraviolet radiation source 108 can be attached using ultraviolet transparent glue, such as the glue 422 shown in FIG. 4C. The ultraviolet transparent glue 422 can be formed of an ultraviolet transparent polymer including a high degree (e.g., at least thirty percent) of ultraviolet transparency such as EFEP, and/or the like. In a preferred embodiment the material is at least 50% transparent.

The ultraviolet radiation source(s) 108 can be located adjacent to any layer of the device 100 and emit radiation at any angle. For example, as shown in FIG. 5A, the device 500 includes the ultraviolet radiation source 108 located on a side of the transparent screen 104. The device 500 can also include a reflecting element 524 located on the opposite side of the ultraviolet radiation source 108. The reflecting element 524 can be configured to redirect any ultraviolet radiation back towards the transparent screen 104 to disinfect the top surface 106. In the embodiment shown, the reflecting element 524 includes a parabolic shaped surface for reflecting the ultraviolet radiation. However, this parabolic shape is for illustrative purposes and it is understood that the reflecting element can be any shape. For example, in FIG. 5B, the reflecting element 624 of the device 600 includes a flat surface for reflecting the ultraviolet radiation. In the embodiment shown in FIG. 5B, the device 600 does not need to include the layer 110 (e.g., air), the plurality of fins 518, or the additional ultraviolet transparent layer 520, which are shown in the embodiment of the device 500 in FIG. 5A. However, these features can be included in the embodiment.

The device can also include a set of detectors (e.g., sensors 38 in FIG. 3). As shown in FIG. 6, the device 700 can include the set of detectors 722, which are located beneath the transparent screen 104. The set of detectors 722 can be configured to detect radiation 724 (e.g., ultraviolet, infrared, visible, microwave, and/or the like). The set of detectors 722 can be attached to the device 700 in a method similar to how the set of ultraviolet radiation sources 108 (FIG. 4C) are attached (e.g., grown or glued on the transparent screen 104). As mentioned herein, ultraviolet transparent glue can be used to attach the set of detectors 722 and/or the set of ultraviolet radiation sources to the device. When the cover 112 is in an open position, and the top surface 106 of the transparent screen 104 is exposed, the detectors 722 can detect an amount and/or type of ambient radiation 724 that the top surface 106 is exposed to. As mentioned herein, the amount and/or type of radiation 724 (ambient and/or emitted by ultraviolet radiation sources 108) that the top surface 106 is exposed to can be used by the monitoring and/or control system 15 (FIG. 2) to control the ultraviolet radiation generated by the set of ultraviolet radiation sources.

Turning now to FIGS. 7A-7C, the device 800 can include a second transparent screen 830 to extend the functionality of the device 800. The second transparent screen 830 can be located between the cover 112 and the transparent screen 104. The second transparent screen 830 can be formed of a material that is substantially the same, or identical to, the material of the transparent screen 104. In the embodiment shown in FIG. 7A, the device 800 includes a set of ultraviolet radiation sources 108 that is located next to the transparent screen 104. However, as discussed herein, the set of ultraviolet radiation sources 108 can be positioned in any layer and at any angle within a device. In the embodiment shown in FIGS. 7B and 7C, some or all of the set of ultraviolet radiation sources 108 are located within the second transparent screen 830. Although the set of detectors 822 are only shown in FIGS. 7B and 7C, it is understood that the embodiment shown in FIG. 7A can also include the set of detectors 822. In FIG. 7A, the cover 112 and the second transparent screen 830 are in a closed position via the hinge 813. In FIG. 7B, the cover 112 and the second transparent screen 830 are in a partially opened position via the hinge 813. In FIG. 7C, the cover 112 and the second transparent screen 830 are in an open position via the hinge 813. In this open position, the second transparent screen 830 can be utilized by a user along with the transparent screen 104, e.g., as part of operating the device 800 (e.g., a smartphone, tablet, and/or the like) in its intended manner.

Figure 8:
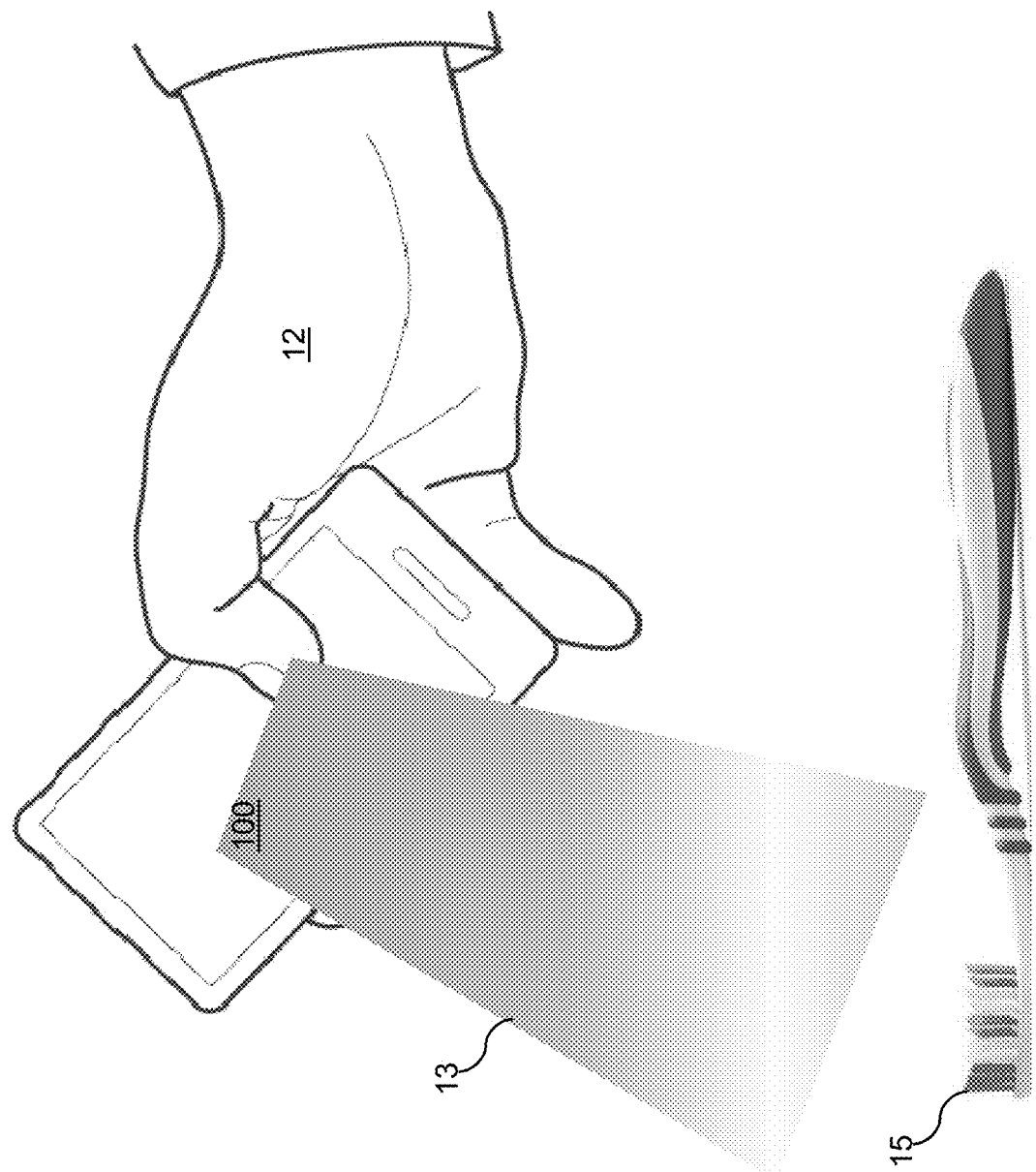
FIG. 8 shows a perspective view of a user implementing an illustrative device as a sterilizing wand according to an embodiment.

In addition to disinfecting a top surface of a device, the ultraviolet radiation system within a device can be used to disinfect other items. For example, as shown in FIG. 8, a user 12 can utilize a device discussed herein, for example, the device 100 shown FIG. 1, to generate ultraviolet radiation 13 directed toward an item 15 in order to disinfect the item 15 (e.g., a toothbrush). In this case, referring to FIG. 3, the computer system 20 can control the set of ultraviolet radiation sources 108 so that when the device 100 is used in this manner, a more focused type of radiation is used so that ultraviolet radiation 13 is only targeted towards the item 15. In contrast, when the device 100 is used to disinfect the top surface 106, a more scattered type of radiation is used so that the top surface 106 is disinfected uniformly and efficiently. In an embodiment, the device 100 can include a first set of ultraviolet radiation sources that are utilized for the focused type of radiation and a second set of ultraviolet radiation sources that are utilized for the scattered type of radiation. Furthermore, the computer system 20 can use data acquired by the feedback component 16 (e.g., visible image data, infrared image data, and/or the like) to ensure that the ultraviolet radiation is being directed onto an object that will not be harmed by the ultraviolet radiation.

Figure 9:
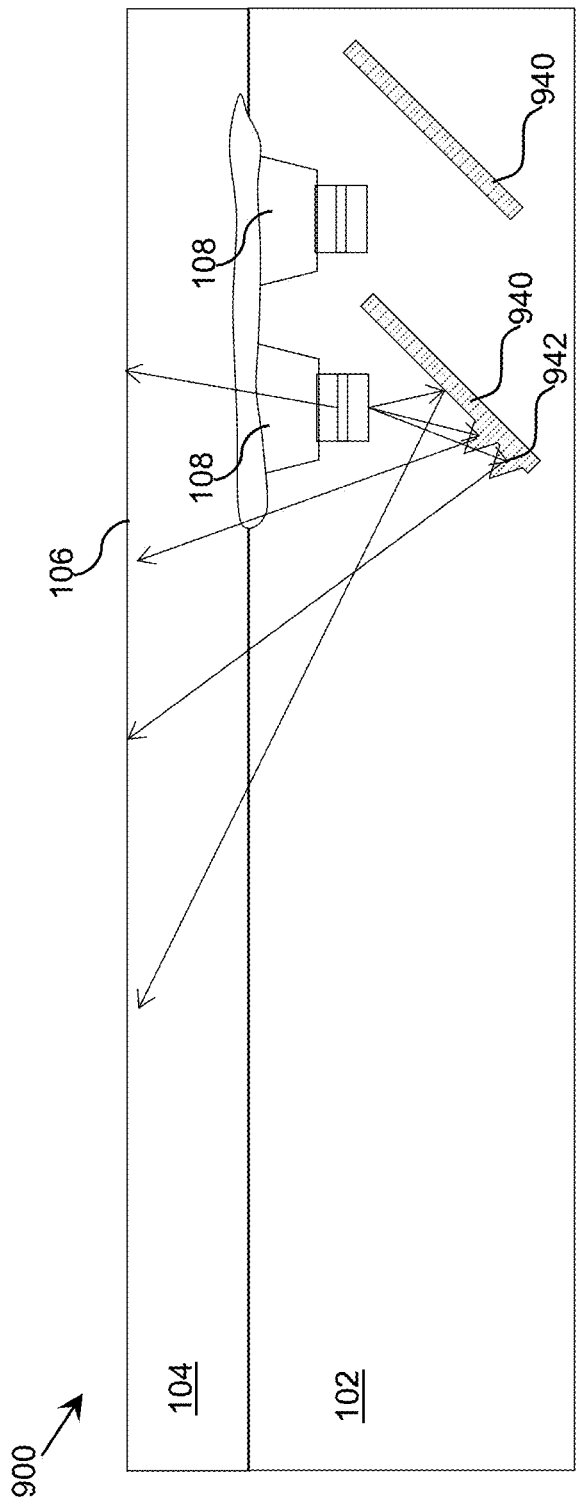
FIG. 9 shows a cross-sectional view of an illustrative device according to an embodiment.

Turning now to FIG. 9, a device 900 can include one or more reflecting elements 940 configured to reflect the ultraviolet radiation towards the top surface 106 of the transparent screen 104. The reflecting element 940 can be formed of any ultraviolet reflecting material, such as polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. In an embodiment, a reflecting element 940 can be located beneath each ultraviolet radiation source 108. In another embodiment, one or more of the reflecting elements 940 can include a set of protrusions 942 to further help in reflecting and/or directing the ultraviolet radiation.

Figure 10:
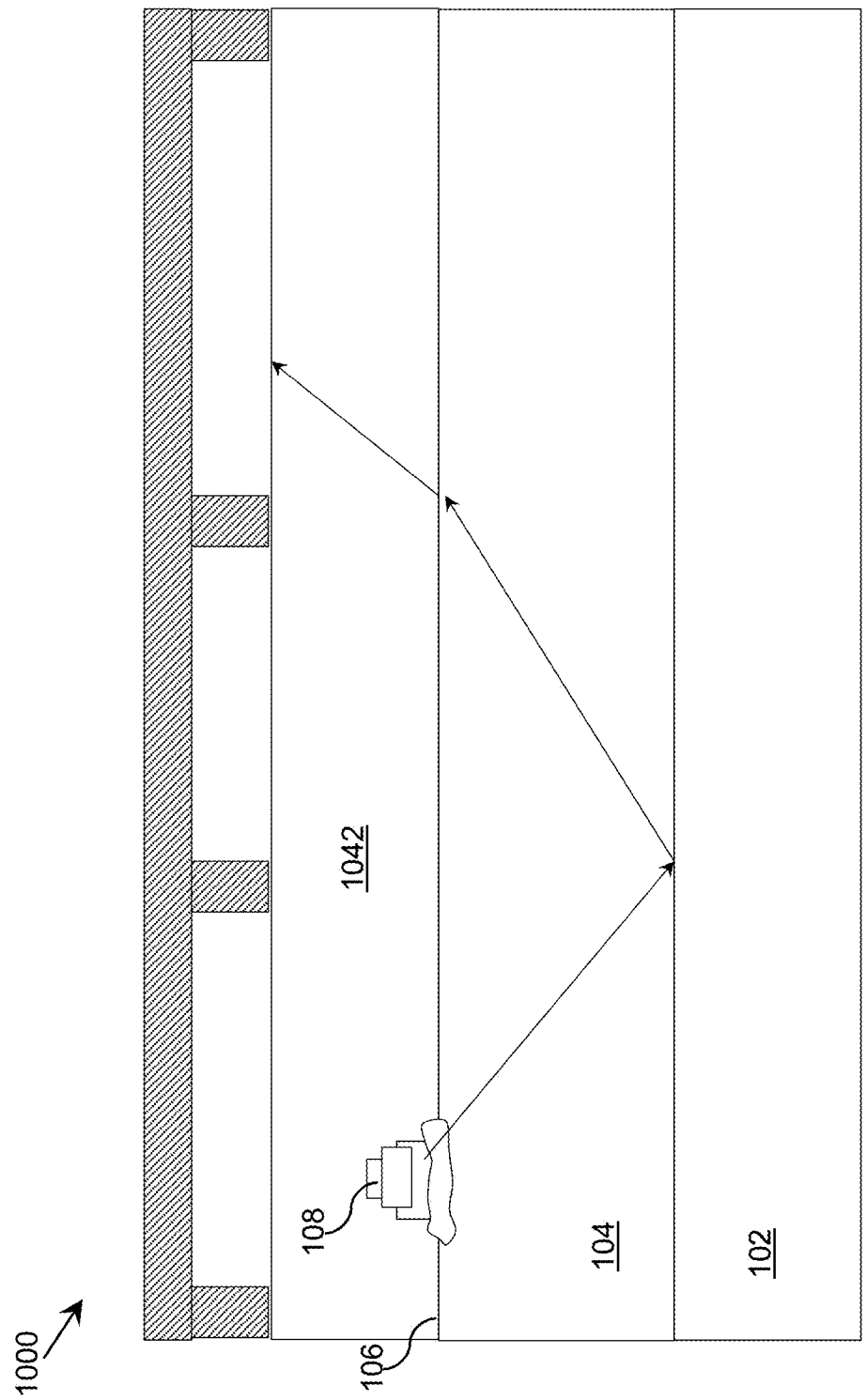
FIG. 10 shows a cross-sectional view of an illustrative device according to an embodiment.

Turning now to FIG. 10, a device 1000 is shown including an ultraviolet transparent protective layer 1042 over the transparent screen 104. In this embodiment, the set of ultraviolet radiation sources 108 can be grown over the top of the transparent screen 104 (e.g., sapphire screen) as long as there is sufficient reflectance at the interface of the transparent screen 104 and the internal portion 102. In an embodiment, the reflectance is at least 20% for sufficient disinfection action. The ultraviolet transparent protective layer 1042 can be formed of an ultraviolet transparent polymer, such as FEP, EFEP, PLA, LDPE, and/or the like. The ultraviolet transparent protective layer 1042 can be provide antireflective and/or screen protection, as well as encapsulating the UV LED source 108.

Turning now to FIGS. 11A and 11B, devices 1100, 1200 can include a roughness component 1150, 1250 configured to improve the light extraction from the set of ultraviolet radiation sources 108. The size of the roughness component 1150, 1250 can be larger or comparable to the wavelength of the ultraviolet radiation generated by the set of ultraviolet radiation sources 108. In FIG. 11A, the roughness component 1150 can be incorporated with the ultraviolet radiation sources 108. For example, a typical ultraviolet radiation device 108 epitaxially grown on a sapphire substrate (e.g., the transparent screen 104) can have a roughness deposited on sapphire surface being a surface opposite to the one where the epitaxial growth has been carried. In FIG. 11B, the roughness component 1250 can be on the top surface 106 of the transparent screen 104.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An apparatus, comprising:
    an ultraviolet transparent structure having an external surface, an internal surface, and side surfaces;
    a set of ultraviolet radiation sources configured to generate ultraviolet radiation towards the external surface of the ultraviolet transparent structure, wherein the set of ultraviolet radiation sources are located away from an edge of the side surfaces of the ultraviolet transparent structure without directly contacting any edge of the side surfaces, wherein an emitting face of each of the ultraviolet radiation sources is at an angle or parallel to the internal surface and the external surface of the ultraviolet transparent structure, and wherein a portion of a surface of the emitting face of each of the ultraviolet radiation sources contacts only one of the internal surface or the external surface of the ultraviolet transparent structure;
    a monitoring and control system to manage the ultraviolet radiation generated from the set of ultraviolet radiation sources by performing a method comprising:
        monitoring a set of attributes relating to the external surface of the ultraviolet transparent structure; and
        controlling, based on the monitoring, the ultraviolet radiation directed at the external surface of the ultraviolet transparent structure; and
    wherein the ultraviolet transparent structure is integrated within a touch screen of an electronic device.

2. The apparatus of claim 1, further comprising a cover configured to cover the external surface of the ultraviolet transparent structure, the cover including an internal surface facing the external surface of the ultraviolet transparent structure that prevents transmission of ultraviolet radiation through the cover.

3. The apparatus of claim 2, wherein the internal surface of the cover comprises a reflective surface, wherein the reflective surface includes an ultraviolet reflective polymer having diffusive reflectivity.

4. The apparatus of claim 2, wherein the cover comprises a plurality of fins extending from the internal surface of the cover, wherein each fin is separated from an adjacent fin by a predetermined spacing, wherein each of the plurality of fins contacts a separate portion of the external surface of the ultraviolet transparent structure in response to the cover being in a closed position, wherein a layer of air is located between the cover and the ultraviolet transparent structure in each spacing formed between adjacent fins.

5. The apparatus of claim 2, further comprising an ultraviolet transparent layer located adjacent to the internal surface of the cover, wherein the cover and the ultraviolet transparent layer removably cover the external surface of the ultraviolet transparent structure.

6. The apparatus of claim 2, further comprising a set of detectors positioned underneath the internal surface of the ultraviolet transparent structure that are configured to detect an amount of radiation adjacent to the external surface of the ultraviolet transparent structure including radiation exposure to the external surface of the ultraviolet transparent structure and ambient radiation exposure to the external surface in response to the cover being in an open position.

7. The apparatus of claim 1, further comprising a set of reflecting elements located adjacent to the set of ultraviolet radiation sources.

8. The apparatus of claim 7, wherein the set of reflecting elements comprise parabolic reflectors.

9. The apparatus of claim 1, further comprising a waveguiding structure to direct and/or deliver emitted radiation from the set of ultraviolet radiation sources towards the external surface of the ultraviolet transparent structure.

10. The apparatus of claim 1, wherein the ultraviolet transparent structure comprises an ultraviolet transparent material, wherein the ultraviolet transparent material comprises at least one of: an ultraviolet transparent polymer or sapphire.

11. The apparatus of claim 1, further comprising a roughness component located adjacent to the set of ultraviolet radiation sources, the roughness component configured to reflect the ultraviolet radiation generated from the set of ultraviolet radiation sources.

12. The apparatus of claim 1, wherein the set of ultraviolet radiation sources emit ultraviolet radiation at multiple distinct peak wavelengths.

13. The apparatus of claim 1, wherein the monitoring of a set of attributes relating to the external surface of the ultraviolet transparent structure comprises: detecting use of the external surface and monitoring a frequency of use of the external surface.

14. The apparatus of claim 1, wherein the monitoring of a set of attributes relating to the external surface of the ultraviolet transparent structure comprises monitoring for a presence of microorganisms and/or contaminants at the external surface.

15. The apparatus of claim 14, wherein the monitoring for a presence of microorganisms and/or contaminants comprises using a visible camera to detect the presence of microorganisms and/or contaminants on the external surface of the ultraviolet transparent structure.

16. The apparatus of claim 15, wherein the visible camera is configured to detect fluorescent signals from microorganisms and/or contaminants that become fluorescent in response to exposure to ultraviolet radiation.

17. The apparatus of claim 1, wherein the monitoring and control system comprises an interface component that permits a user to control operation of the set of ultraviolet radiation sources.

18. The apparatus of claim 1, wherein the monitoring and control system comprises an ultraviolet indicator that provides an indication that the set of ultraviolet radiation sources are activated and generating ultraviolet radiation.

19. A device, comprising:
   an ultraviolet transparent structure having an external surface, an internal surface, and side surfaces;
   a set of ultraviolet radiation sources configured to generate ultraviolet radiation directed towards the external surface of the ultraviolet transparent structure, wherein the set of ultraviolet radiation sources are located away from an edge of the side surfaces of the ultraviolet transparent structure without directly contacting any edge of the side surfaces, wherein an emitting face of each of the ultraviolet radiation sources is at an angle or parallel to the internal surface and the external surface of the ultraviolet transparent structure, and wherein a portion of a surface of the emitting face of each of the ultraviolet radiation sources contacts only one of the internal surface or the external surface of the ultraviolet transparent structure;
   a cover configured to cover the ultraviolet transparent structure, the cover including an internal surface facing the external surface of the ultraviolet transparent structure that prevents transmission of ultraviolet radiation through the cover; and
wherein the ultraviolet transparent structure is integrated within a touch screen of an electronic device.

20. A cover for an electronic device, comprising:
   an ultraviolet transparent structure configured for integration with a touch screen of the electronic device, the ultraviolet transparent structure having an external surface, an internal surface, and side surfaces, wherein the external surface of the ultraviolet transparent structure is configured to provide covering to the touch screen;
   a set of ultraviolet radiation sources configured to generate ultraviolet radiation directed towards the touch screen via the external surface of the ultraviolet transparent structure, wherein the set of ultraviolet radiation sources is located away from an edge of the side surfaces of the ultraviolet transparent structure without directly contacting any edge of the side surfaces, wherein an emitting face of each of the ultraviolet radiation sources is at an angle or parallel to the internal surface and the external surface of the ultraviolet transparent structure, and wherein a portion of a surface of the emitting face of each of the set of ultraviolet radiation sources contacts only one of the internal surface or the external surface of the ultraviolet transparent structure; and
   a monitoring and control system to manage the ultraviolet radiation generated from the set of ultraviolet radiation sources by performing a method comprising:
      monitoring a set of attributes relating to the external surface of the ultraviolet transparent structure; and
      controlling, based on the monitoring, the ultraviolet radiation directed at the external surface of the ultraviolet transparent structure.

* * * * *